(12) United States Patent
Briscoe et al.

(10) Patent No.: US 7,534,395 B2
(45) Date of Patent: May 19, 2009

(54) HYSTERESIS COMPENSATION SYSTEM

(75) Inventors: Matt Briscoe, Indianapolis, IN (US);
Rick Spencer, Indianapolis, IN (US);
Jonn R. Hitch, Indianapolis, IN (US);
Chad Buckles, Zionsville, IN (US)

(73) Assignee: Beckman Coulter, Inc., Fullerton, CA (US)

( * ) Notice: Subject to any disclaimer, the term of this patent is extended or adjusted under 35 U.S.C. 154(b) by 409 days.

(21) Appl. No.: 10/832,663

(22) Filed: Apr. 27, 2004

(65) Prior Publication Data

US 2005/0238544 A1    Oct. 27, 2005

(51) Int. Cl.
*G01N 15/06* (2006.01)
*G01N 21/77* (2006.01)
*B01L 3/02* (2006.01)
*H02P 23/00* (2006.01)
*G01F 25/00* (2006.01)

(52) U.S. Cl. ............... 422/100; 422/68.1; 318/701; 73/1.74; 436/169

(58) Field of Classification Search ............. 192/21, 192/21.5; 422/100, 68.1; 425/135; 73/864.21, 73/1.74; 318/701; 436/169
See application file for complete search history.

(56) References Cited

U.S. PATENT DOCUMENTS

| | | | |
|---|---|---|---|
| 3,146,620 A * | 9/1964 | Morrill, Jr. ............ 73/149 |
| 4,117,727 A * | 10/1978 | Friswell et al. ......... 73/19.02 |
| 4,207,770 A | 6/1980 | Brushow |
| 4,407,659 A | 10/1983 | Adam |
| 4,478,095 A * | 10/1984 | Bradley et al. ........ 73/864.21 |
| 4,519,258 A | 5/1985 | Jakubowicz |
| 4,539,854 A | 9/1985 | Bradshaw et al. |
| 4,540,359 A * | 9/1985 | Yamazaki ............ 425/135 |
| 4,772,830 A * | 9/1988 | Kobari et al. ........... 318/563 |
| 4,833,384 A | 5/1989 | Munro et al. |
| 4,938,087 A | 7/1990 | Ragard |
| 5,183,150 A | 2/1993 | Chary et al. |
| 5,219,099 A | 6/1993 | Spence et al. |
| 5,238,095 A * | 8/1993 | Pedu ..................... 192/84.1 |
| 5,296,194 A | 3/1994 | Igarashi |
| 5,336,467 A | 8/1994 | Heidt et al. |
| 5,337,608 A | 8/1994 | Egan et al. |
| 5,360,596 A | 11/1994 | Pennatto |
| 5,531,131 A | 7/1996 | Sabloewski |
| 5,600,194 A | 2/1997 | Toukola |
| 5,608,394 A * | 3/1997 | Hirabayashi ............ 341/11 |
| 5,635,622 A | 6/1997 | King |
| 5,792,483 A * | 8/1998 | Siegrist et al. .......... 425/135 |
| 6,170,340 B1 | 1/2001 | Horiuchi et al. |
| 6,178,295 B1 * | 1/2001 | Nakata et al. ........... 396/103 |
| 6,244,395 B1 | 6/2001 | Schlagenhaft |
| 6,257,380 B1 | 7/2001 | Duncan |

(Continued)

*Primary Examiner*—Jill Warden
*Assistant Examiner*—Lore Ramillano
(74) *Attorney, Agent, or Firm*—Morrison & Foerster LLP

(57) ABSTRACT

A system and method for compensating for hysteresis in laboratory liquid handling apparatus. The system comprises a carriage holding a drive gear that meshes with and drives a gear rack. A hysteresis brake is also provided on the carriage and opposes the movement of the drive gear to provide continued positive engagement of the drive gear with the gear rack even when the system is static. When the direction of travel of the gear rack is reversed, the drive gear rotates an additional distance that compensates for the aggregate hysteresis found in the drive train.

8 Claims, 8 Drawing Sheets

U.S. PATENT DOCUMENTS

| | | |
|---|---|---|
| 6,347,259 B1 | 2/2002 | Goldenberg et al. |
| 6,595,453 B2 | 7/2003 | Dürrstein et al. |
| 2002/0119076 A1* | 8/2002 | Dean et al. ................. 422/68.1 |
| 2003/0155821 A1 | 8/2003 | Frissen et al. |
| 2005/0158076 A1* | 7/2005 | Pichlmeier et al. .......... 399/165 |

* cited by examiner

HYSTERESIS COMPENSATION SYSTEM

BACKGROUND

The present invention relates to a method and apparatus for economically ensuring the precise and reproducible automation of laboratory instrumentation. Particularly, the present invention relates to precision movement of laboratory instrumentation such as pipette tips in a manner that overcomes hysteresis inherent in gear-driven positioning mechanisms.

Automated laboratory handling systems require precise, repeatable movements to be made in a predictable manner, as the machinery used must meter out very small amounts of liquid and move within extremely small microplate wells with precision and accuracy. Laboratory pipetting systems, in particular, must be precisely controlled to move in the X, Y, and Z planes in order to position a bank of micropipette tips into the bottom of corresponding microplate wells. If a pipette tip is not inserted deeply enough into a well, a sufficient amount of the liquid may not be removed, potentially compromising the test or reaction. Further, if the pipette tip is inserted too deeply, damage could result to the pipette tip or delivery apparatus. Creating machinery with this type of predictability of movement is difficult due to the fact that numerous components comprising any mechanical system have a certain amount of imprecision in their fit with one another. When aggregated into a final assembly, an unpredictable amount of "play" in the final movement of the machinery occurs, often referred to as hysteresis. The presence of hysteresis indicates the inability to predict the exact location of a given component, which could result in broken instrumentation, reduced ability to uptake or adequately measure a given chemical in a chemical well, or contamination of a sample.

Reduction of hysteresis is often accomplished by utilizing highly precise components such as precision ground gears and precision servo motors, or by utilizing expensive position sensing systems. These methods leave much to be desired, as the components add substantial sums to the final cost of a system, and precision gears must be routinely replaced to account for the reduction in precision as friction takes its toll on the components. Further, although precision components are subject to a very small maximum value of error, the amount of error is not consistently the same. Therefore, these conventional methods of reducing hysteresis in mechanical devices result in high costs that do not necessarily guarantee precision or predictability.

Therefore, an efficient, reliable and low-cost hysteresis compensation device operable to reduce slop, play, or backlash associated with positioning laboratory equipment is desired.

SUMMARY

The present invention relates to economically ensuring the precise and reproducible automation of laboratory instrumentation. According to one embodiment of the present invention, an apparatus for reducing hysteresis in an automated laboratory device includes a liquid handling system that comprises a gear rack, a chassis assembly having at least one drive gear operable to engage the gear rack, and at least one hysteresis brake that engages the gear rack and resists rotation, thereby maintaining positive engagement of the drive train. This embodiment could further comprise a pipette assembly. Additionally, the embodiment could be arranged such that the hysteresis brake is positioned on the chassis assembly. Finally, the hysteresis brake in this embodiment could be a magnetic brake or an electromagnetic brake.

According to a second embodiment of the present invention, an apparatus for providing precision linear positioning of at least one laboratory pipette comprises a rack, a drive mechanism having a drive component operable to engage a linear rack, a magnetic brake engaging the rack operable to provide a force opposing movement of the drive mechanism. The second embodiment could further comprise a carriage assembly holding the drive mechanism and the magnetic brake. Further, the second embodiment could additionally comprise a pipette connected to the gear rack or the carriage assembly.

A third embodiment of the present invention could comprise an apparatus for increasing precision in liquid handling systems comprising a drive motor connected to a first gear, a rack in contact with the first gear, and a second gear equipped with a magnetic brake operable to provide a force opposing movement of the first gear. Additionally, this apparatus could further comprise software which can control the drive motor. Further, the software controlling the drive motor could adjust the work output of the motor so that the error margin of the apparatus is compensated when reversing direction of the drive motor.

A fourth embodiment of the present invention is a method for compensating hysteresis in laboratory liquid handling systems comprising the steps of providing a carriage with a drive gear that engages a linear gear rack; providing a motor in connection with the drive gear via a drive train; providing a hysteresis brake engaging the gear rack; adjusting the hysteresis brake so that resistance is provided to movement of the gear rack, causing the drive gear to remain in positive engagement with the gear rack; and engaging the motor so that the drive train is positively engaged, causing the drive gear to move the gear rack in a first direction. Additionally, this method could include the step of reversing the motor so that the drive gear moves the gear rack in a second direction. Further, after reversing the motor, the method could include the step of calculating an error margin caused by play in the drive train components involved in reversing direction of the gear rack. Finally, the method could include the step of compensating for the error margin that occurs by rotating the motor a calculated distance directly related to the error margin. The calculation of the error margin and compensation for the error margin could be accomplished by using a software program.

DESCRIPTION

The present invention relates to laboratory precision automation of instrumentation. More specifically, the invention relates to a laboratory pipetting system designed to operate in a manner such that positioning the automated pipette can be done predictably and reliably in an exact manner.

Figure 1:
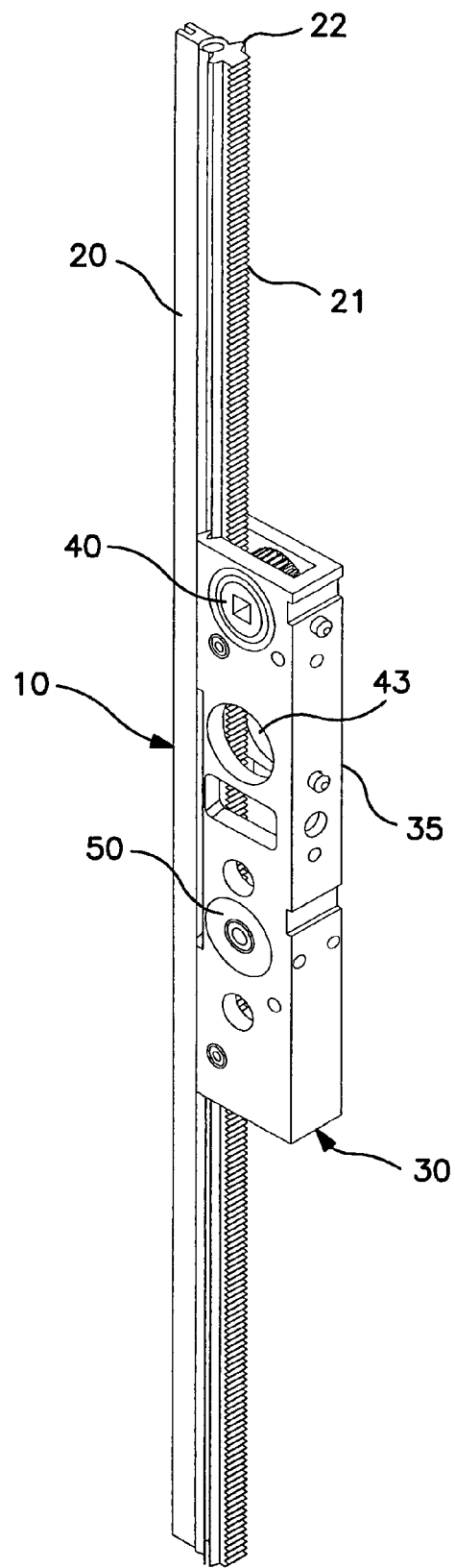
FIG. 1 shows a perspective view of one embodiment of a pipette drive assembly with a hysteresis compensation mechanism.

Turning now to FIG. 1, a pipette drive assembly 10 according to one embodiment of the present invention comprises a gear rack 20 and a carriage assembly 30 engaging gear rack 20 such that carriage assembly 30 is operable to move relative to gear rack 20. Gear rack 20 comprises a linear member having gear teeth 21 along one side and a ridge 22 on either side of the gear teeth. Carriage assembly 30 comprises chassis 35, drive gear 40, pass-thru holes 43, and hysteresis brake 50. Further, drive gear 40 engageably contacts gear rack 20, and hysteresis brake 50 likewise engages gear rack 20.

Figure 2:
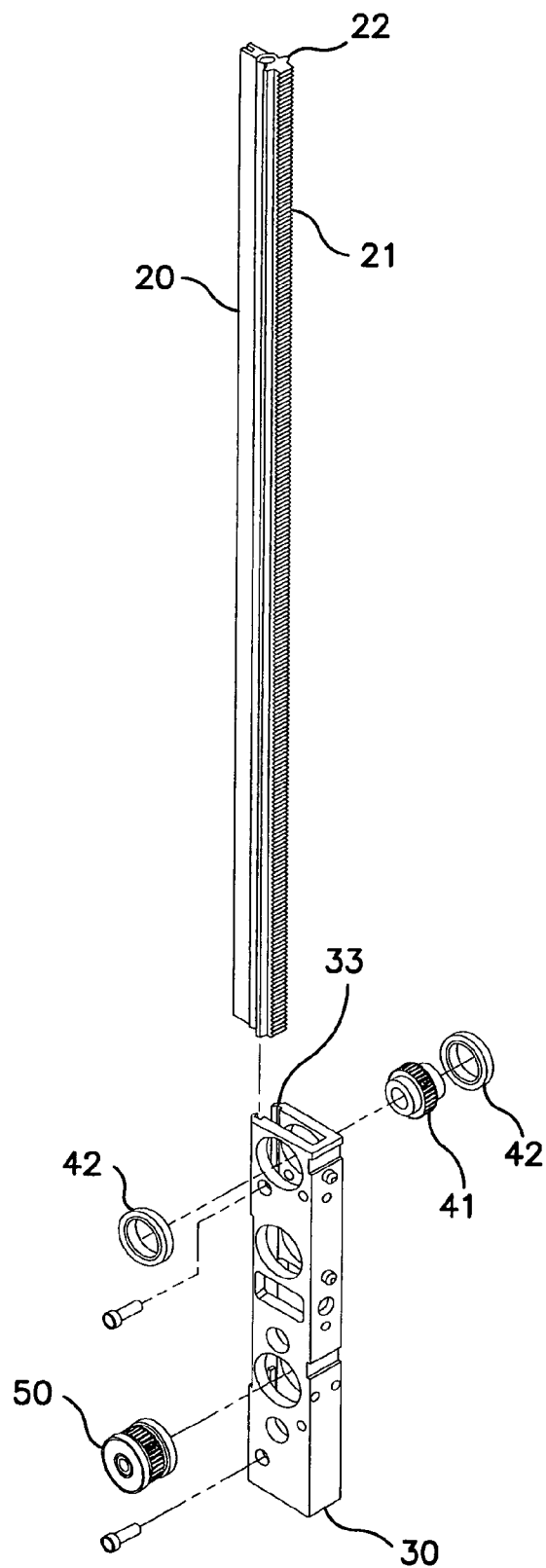
FIG. 2. shows an expanded perspective view of the pipette drive assembly of FIG. 1.

FIG. 2 shows an expanded view of pipette drive assembly 10 according to one embodiment of the present invention. As shown herein, the relationship between the gear teeth of drive gear assembly 40 and hysteresis brake 50 is more readily discernable. Drive gear 41 comprises multiple gear teeth which engageably mesh with the gear teeth 21 of gear rack 20 when carriage assembly 30 is engageably mounted to gear rack 20. Carriage assembly 30 includes channels 33 that slidably engage the ridges 22 of gear rack 20 in a manner that properly orients the carriage assembly 30 with respect to the gear rack 20 and ensures that gear teeth 21 of gear rack 20 are a proper distance from the drive gear 41 to engage the teeth of the drive gear. Drive gear 41 includes a rectangular bore through its central axis designed to receive a drive shaft from a drive motor that provides torque to turn the drive gear 41. Hysteresis gear 51 of hysteresis brake assembly 50 also has teeth which engageably mesh with the teeth 21 of gear rack 20 when carriage assembly 30 is engageably mounted to gear rack 20. Therefore, drive gear assembly 40, if rotatably attached to a motor or some other turning force is operable to move gear rack 20 in a linear fashion relative to carriage assembly 30.

Figure 7:
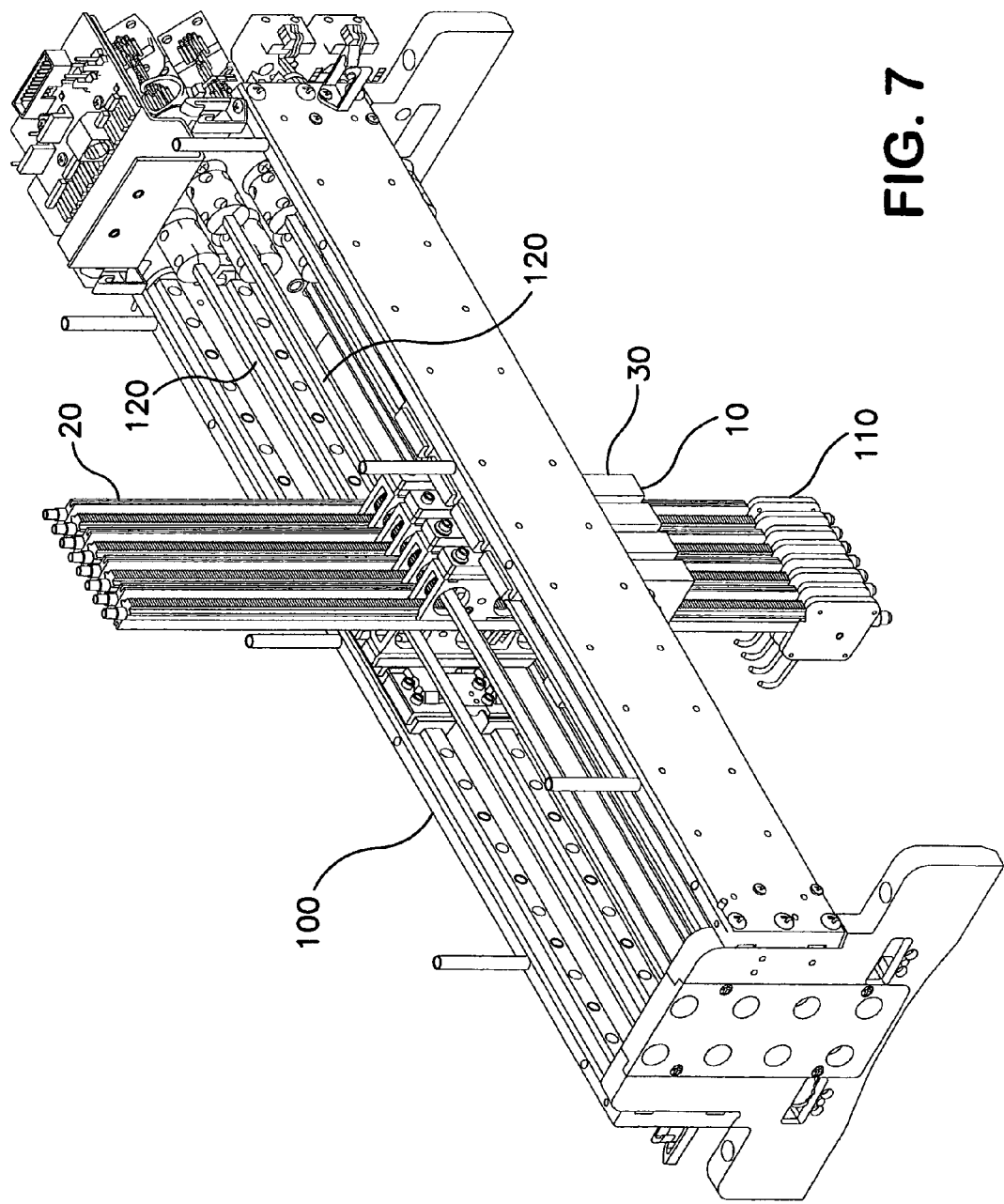
FIG. 7 shows a perspective view of a pipette drive system having multiple pipettes.

In one embodiment such as that shown in FIG. 7, a drive train connects an electric motor to drive gear assembly 40. The drive train comprise a motor, a drive shaft in the form of a square shaft extending through the center rectangular bore of drive gear assembly 40. In operation, the motor is signaled to rotate in a particular direction, causing adjoining square drive shaft to likewise turn and rotate drive gear assembly 40. By the means described above, the rotation of drive gear assembly 40 causes gear rack 20 to move relative to carriage assembly 30. Any number of additional drive components could also be used to provide translation of a force from the electric motor to the carriage assembly or rack, causing movement. Each permutation of a drive train or drive mechanism would transfer a force into movement of the carriage assembly or rack. However, each connection point or component within the drive train offers an addition of mechanical play where hysteresis is introduced.

Figure 3:
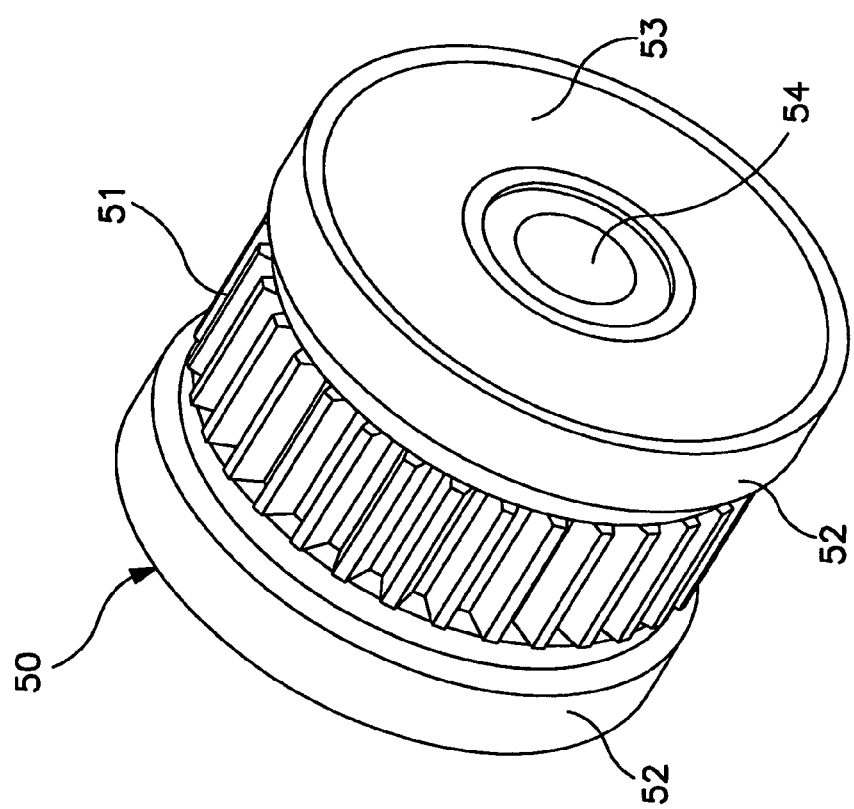
FIG. 3 shows a perspective view of the magnetic hysteresis brake shown in FIG. 1.
Figure 4:
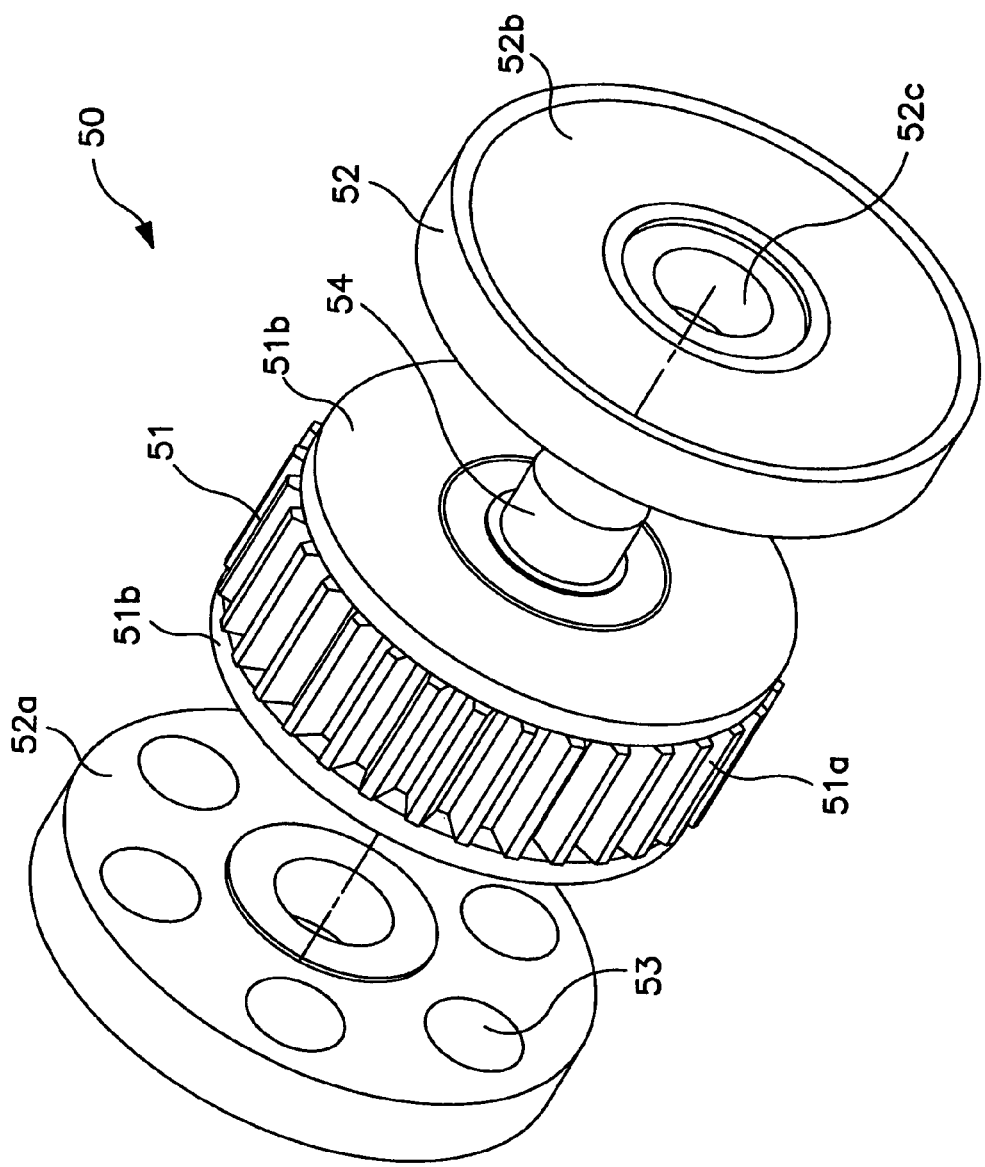
FIG. 4 shows an expanded view of the magnetic hysteresis brake of FIG. 3.

FIG. 3 shows a perspective view of hysteresis brake assembly 50, a component of pipette drive assembly 10 shown in FIGS. 1 and 2. FIG. 4 shows an expanded view of the magnetic hysteresis brake assembly 50 of FIG. 3. As shown in FIGS. 3 and 4, hysteresis brake assembly 50 comprises hysteresis gear 51 sandwiched between two mounting plates 52. Each mounting plate includes an inner face 52a directed toward the hysteresis gear 51 and an outer face 52b directed away from the hysteresis gear 51. A plurality of magnets 53 are positioned around the inner face 52a of the mounting plates 52. The hysteresis gear 51 includes a circular toothed gear portion 51a positioned between two circular metal side plates 51b. An attached axle 54 extends from the center of both sides of the circular toothed gear portion, such that rotation of the toothed gear portion 51a results in rotation of the axle 54. Each mounting plate 52 includes a bushing 52c designed to support axle 54 and allow rotation of the axle relative to the mounting plates 52. The mounting plates 52 are fixed to the carriage allow hysteresis brake assembly 50 to be rotatably mounted to carriage assembly 30. In operation of the hysteresis brake, the magnets 52 on the mounting plates 52 are attracted to the metal side plates 51b. This magnetic attraction acts to provide a force that resists rotation of the metal side plates 51b and attached hysteresis gear 51 relative to the mounting plates 52. Hysteresis brake assembly 50 is representative of several commercially available assemblies, of which Magnetic Technologies Ltd. of Oxford, Mass. is one manufacturer. Functionally, hysteresis brake assembly 50 operates to resist rotation of hysteresis gear 51 because rotation thereof causes internal magnets 53 to rotate through lines of magnetic force.

Figure 8:
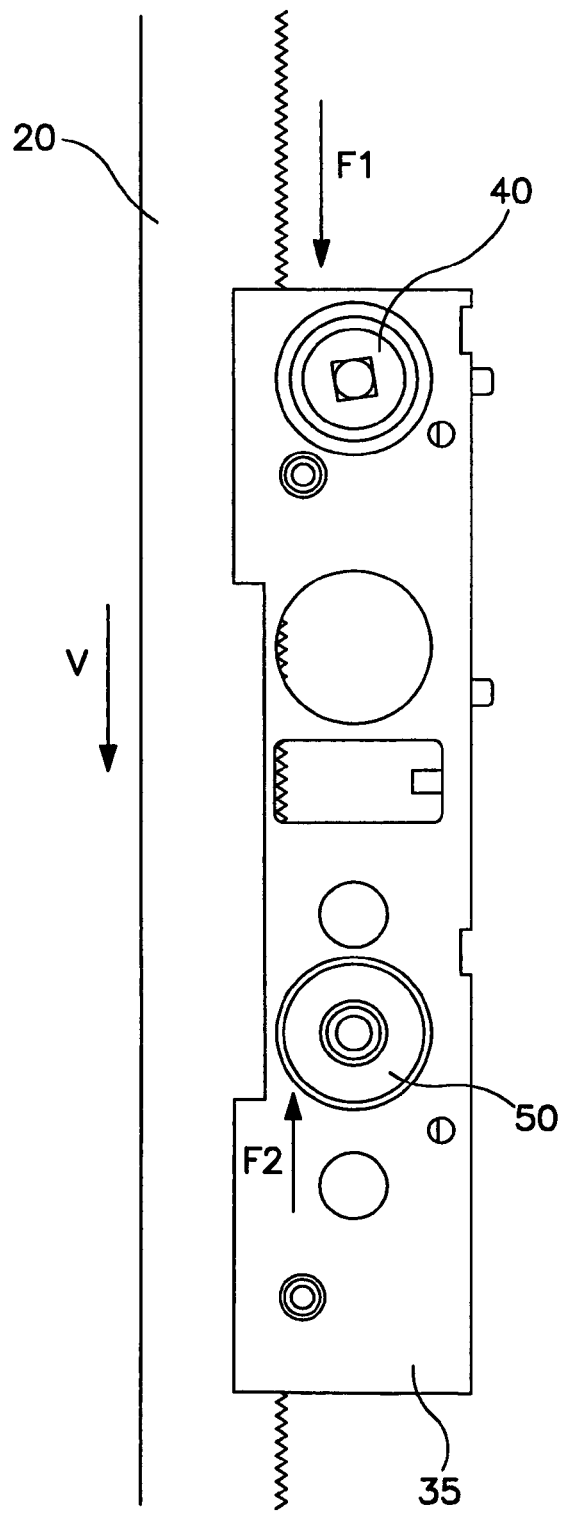
FIG. 8 shows a diagram of the basic force/velocity vectors involved when the pipette drive system with hysteresis compensation mechanism is in motion.

In operation, hysteresis gear 51 engages gear rack 20 and rotates axle 54 as gear rack 20 is moved relative to carriage assembly 30. According to the orientation of FIG. 1, as gear rack 20 is driven downward by counter-clockwise rotation of drive gear 40, carriage assembly 30 remains static. During this action, hysteresis gear 51 of hysteresis brake assembly 50 rotates with axle 54 in a counter-clockwise fashion. Likewise, as gear rack 20 is driven upward, carriage assembly 30 remains static, and hysteresis gear 51 rotates clockwise with axle 54. Because the magnets of the hysteresis brake assembly 51 resist rotation of the hysteresis gear, hysteresis gear assembly provides a braking force that resists movement of the gear rack 20 relative to the carriage assembly 30. FIG. 8 provides a graphical display of the this braking force. In particular, FIG. 8 shows the gear rack 20 moving downward with respect to the chassis 35 at a given velocity (v) and with a driving force (F1) applied by drive gear assembly 40. As the gear rack 20 moves downward, the hysteresis brake 50 resists movement of the gear rack 20 relative to the chassis 35, which results in an upward force (F2) applied to the gear rack. When the drive gear stops rotating, the downward driving force (F1) is removed from the gear rack. However, the upward force from the hysteresis brake remains. Accordingly, all components of the drive train remain completely engaged. If the upward force from the hysteresis brake 50 were absent, stopped movement of the gear rack would result in introduction of hysteresis back into the drive system, and that hysteresis would have to be compensated before the gear rack would start to move following the stop.

Because hysteresis brake 50 is operable to resist linear movement of gear rack 20 relative to carriage assembly 30, a force greater than the resistance of hysteresis brake 50 must be applied to drive gear 41 in order to move gear rack 20. Further, because the resistance of hysteresis brake 50 remains relatively constant, and because the resistance of hysteresis brake 50 is greater than external forces which might otherwise disengage the drive components of the drive train (e.g., gravity, momentum), the drive train remains in "positive engagement" even when the drive train comes to a stop. The term "positive engagement" as used herein refers to the state of the drive train where each of the drive train components remain sufficiently engaged such that incremental rotation of the motor will result of equivalent movement of the driven device with little or no mechanical play or hysteresis between the components. Therefore, when the drive train is in "positive engagement", the teeth of drive gear 41 remain fully engaged and in positive contact with the teeth 21 of the gear rack 20 such that incremental rotation of the drive gear 41 results in equivalent movement of the gear rack 20 with no play between the teeth. Furthermore, when the drive train is once again powered after coming to a stop, the teeth of drive gear 41 remain in positive contact with the teeth of gear rack 20, provided the rotation of drive gear 41 remains in the same direction as the direction of travel prior to coming to a stop. Additionally, the constant resistance of hysteresis brake 50 during a stop likewise ensures positive contact of all components of the drive train, not just the teeth of the drive gear and gear rack. Thus, because hysteresis is not introduced into the drive train during a stop, the play between drive train components is removed and the distance carriage assembly 30 is moved for every rotation of drive gear 41 remains constant (again, provided that the new direction of drive train travel is the same as the previous direction of drive train travel). Thus, rotation of drive gear 41 results in movement of gear rack 20 in a predictable and precise manner.

Figure 5:
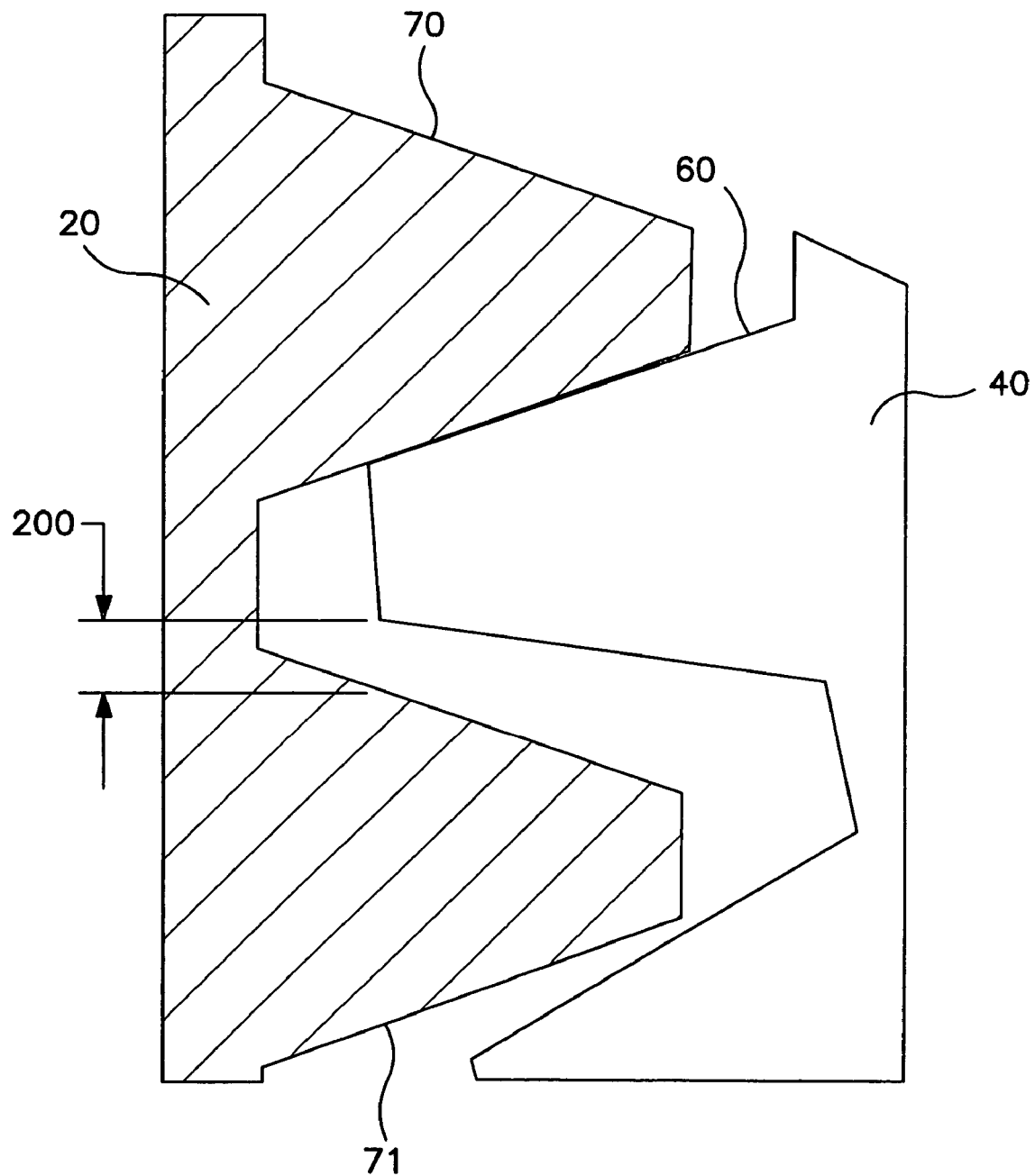
FIG. 5 shows cross-sectional view of the interaction of the gear teeth of the gear rack and the drive gear of the pipette drive assembly of FIG. 1.

As set forth in the preceding paragraph, the resistance caused by hysteresis brake 50 retains positive engagement of the teeth of drive gear 41 with the gear teeth of gear rack 20. Positive engagement remains while drive gear 41 turns in one direction and remains provided that the drive gear 41 stops and continues in the same direction as its previous direction. As discussed previously, this positive engagement remains because of the resistive force provided by the hysteresis brake. However, if the direction of the drive train is ever reversed, the hysteresis inherent in the drive train will be introduced into the system once again. An example of such hysteresis can be seen with respect to FIG. 5. As shown in FIG. 5, if the rotation of drive gear 41 is reversed from clockwise rotation to counter-clockwise rotation, the tooth 60 of drive gear 41 must rotate an additional distance 200 before the first tooth 70 of the gear rack 20 is disengaged and the second tooth 71 of gear rack 20 is fully engaged. Once drive gear tooth 60 moves the additional distance 200 and engages second gear rack tooth 71 positive engagement of drive train is again achieved. This additional distance 200 provides an example of the hysteresis that may be found between drive train components. Of course, similar hysteresis may be found between other drive train components, which results in an aggregated error margin or total hysteresis of the drive system. Fortunately, the total hysteresis of the drive system when the drive train switches direction can be calculated with reasonable accuracy. Because play between gear teeth is isolated to a predictable distance that occurs only upon a change in direction of the drive gear 41, movement of carriage assembly can be precisely calculated and repeated, and hysteresis is eliminated or greatly reduced.

As set forth above, hysteresis brake 50 ensures positive engagement of each mechanical junction of any drive train components as long as the motor is turned in the same direction.

Further, positive engagement in one direction ensures that when motor direction is reversed, the distance motor turns before positive engagement returns is repeatable. This repeatable, predictable distance, referred to herein as the "error margin," can be calculated through calibration of the machinery to determine the distance the motor must rotate before positive engagement is reinstated. Further, the error margin can be calibrated and compensated through a software program or other means. Since the error margin is predictable after it has been calculated, the computer program can instruct the motor driver to rotate the motor the distance related to the error margin when the direction of the drive train is reversed. This additional distance compensate for play between the drive train components when the direction of the drive train is reversed and positively engages the drive train in the reversed direction. Having compensated for the error margin, the motor may be rotated a distance sufficient to drive driven component a requested distance of travel when the drive train components are in positive engagement.

Figure 6:
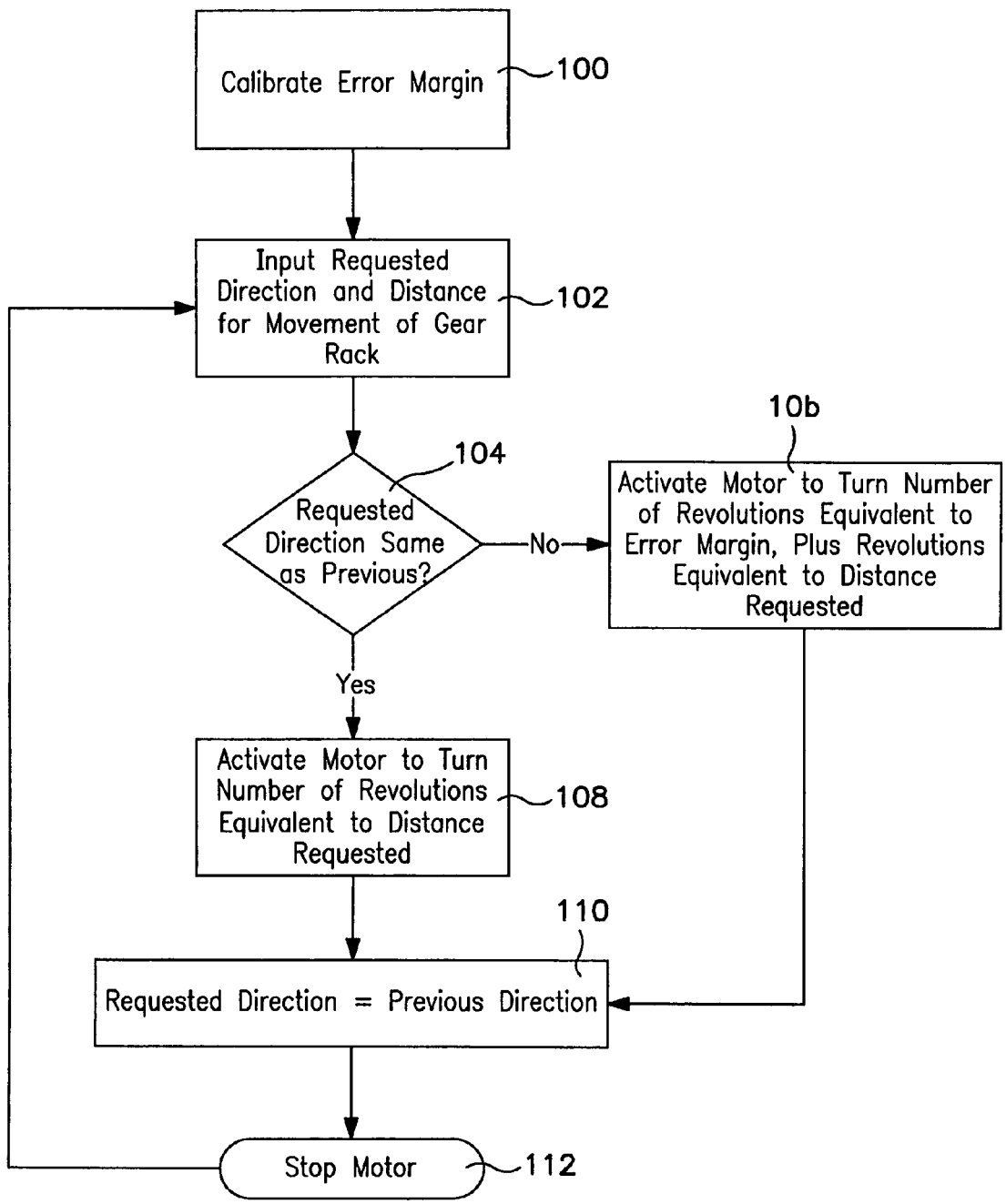
FIG. 6 shows a block diagram of a method for compensating for hysteresis in a liquid handling system.

FIG. 6 is a flow chart delineating one embodiment of a method for compensating for the predictable error margin in moving gear rack 20 in relation to carriage assembly 30. As can be seen from FIG. 6, before the system is put in use, the error margin (or total hysteresis) is first calibrated, either manually or through the use of software, as noted by reference numeral 100. This error margin reflects the amount of hysteresis between positive engagement of the drive train in one direction and positive engagement of the drive train in the opposite direction. With this error margin, the software calculates the amount of motor rotation required in order to switch from a condition of positive engagement of the drive train in one direction and positive engagement of the drive train in the opposite direction (i.e., the amount of motor rotation required before the gear rack 20 is moved when the drive train switches directions). Once the error margin is calculated, the system is ready for normal operation and is operable to allow for compensation of the error margin upon reversal of direction.

In normal operation, as indicated by reference numeral 102 in FIG. 6, the software receives some input from the user of the system for the drive train to move a driven component (e.g., the gear rack and associated pipette) a requested direction of travel and distance of travel. As indicated by reference numeral 104, the system then determines if the requested direction is the same as the previous direction of travel of the drive train. If the requested direction is the same direction as the previous direction, each turn of the motor results in the movement of gear rack 20 a given distance in relation to carriage assembly 30, as noted by reference numeral 108. As discussed above, precise determination of the number of rotations required for the drive motor to move the gear rack a desired distance is possible because the hysteresis brake maintains positive engagement of the drive train elements while the drive train is stopped. Therefore, when the requested direction is the same direction as the previous direction, any incremental rotation of the drive motor results in a related movement of the gear rack. On the other hand, as indicated by reference numeral 106, if the requested direction is different from the previous direction of drive train movement, the calculated error margin is added to the rotations that would otherwise be required to move the gear rack the desired distance. Therefore, by recognizing whether the direction requested is the same or opposite from the previous direction requested, the software can determine whether the error margin must be calculated in the number of turns the motor is to make. If the direction requested is the same as the previous direction the motor was moving, no error margin should be included in the calculation of the number of turns the motor is to make. However, if the direction requested is not the same as the previous direction the motor was moving, the software will compensate for the error margin by turning the motor in the new direction the calibrated number of turns necessary for positive engagement in the new direction. Additionally, the program will calculate and execute the number of turns the motor must make in the new direction to move gear rack 20 the distance requested in relation to carriage assembly 30. Thereafter, as indicated by reference numeral 110 the software resets the previous direction indicator to equal the most recently requested direction of travel. Finally, as indicated by reference numeral 112, the program stops the motor and awaits further instruction on a desired direction of travel and distance of travel.

Turning now to FIG. 7, one embodiment of a pipette system with a hysteresis compensation mechanism includes eight pipette drive assemblies 10 ganged together in a vertical position. Each pipette drive assembly includes a carriage assembly 30 fixed in position vertically and operably joined to a gear rack 20 such that the gear racks 20 may be moved vertically with respect to the carriage assemblies 30. The gear racks 20 and associated carriage assemblies 30 are arranged in two separate rows, with the gear racks on the first row rotated 180° from the gear racks on the second row. A horizontal rack assembly 100 is operable to move the ganged pipette drive assemblies 10 in the horizontal plane. Attached to the bottom of each gear rack assembly 20 is a pipette connector 110, designed for attachment to pipette tips and operable to pipette liquids. Each carriage assembly has an associated drive motor positioned upon the horizontal rack assembly. An elongated drive shaft 120 extends from each drive motor. Each elongated drive shaft 120 engages the drive gear assembly 40 on one of the carriages and extends through the pass-thru holes 43 of the other carriages in the row. In this embodiment, rotation of the drive gears 41 results in linear movement of gear racks 20 either upward or downward. Also, because each gear rack 20 and associated carriage assembly 30 is connected to a different motor and drive shaft 120, each gear rack 20 and the pipette connected thereto may be moved independent of the other gear racks and pipettes.

Although the present invention has been described in considerable detail with reference to certain preferred versions thereof, other versions are possible. For example, a hysteresis brake as described above could be used in conjunction with a drive gear engaging another circular gear to prevent play and backlash. Further, gear rack 20 could be held stationary while carriage assembly 30 moves along gear rack 20. Other embodiments of drive mechanisms engaging a rack are further possible. For example, rubber wheels could be used in place of gears. Additionally, means for resisting movement could comprise springs, elastic bands or rubber bands to resist movement of components and ensure positive engagement. As another example, any number of different pipette systems may be used with the Hysteresis Compensation System. For example, the system shown in FIG. 7 could include gear racks that are 180° opposed to the gear racks shown. As another example, any number of gear racks and associated pipettes could be used in any one system. Furthermore, the present invention is not limited to liquid handling systems, but may be used for any number of other automated laboratory devices where a motor and a drive train is used to automatically advance a driven component. Therefore, the spirit and scope of the appended claims should not be limited to the description of the preferred versions contained herein.

What is claimed is:

1. A method for operating an automated laboratory device comprising the steps of:
   a. providing a drive gear that engages a linear gear rack;
   b. providing a motor in connection with said drive gear via a drive train;
   c. providing a hysteresis brake engaging said linear gear rack;
   d. engaging the motor such that said drive train is positively engaged, causing said drive gear to move the gear rack in a first linear direction relative to the drive gear;
   e. applying the hysteresis brake during engagement of the motor such that resistance is provided to movement of the gear rack in the first linear direction relative to the drive gear whenever the gear rack is moved in the first linear direction relative to the drive gear, the hysteresis brake causing the drive gear to remain in positive engagement with the gear rack following movement of the gear rack in the first linear direction relative to the drive gear.

2. The method of claim 1 further comprising the step of reversing the motor, such that said drive gear moves said gear rack in a second direction.

3. The method of claim 2 further comprising the step of calculating an error margin caused by play in the drive train components involved in reversing direction of said gear rack.

4. The method of claim 3 further comprising the step of compensating for the error margin occurring when the direction of said gear rack is reversed by rotating said motor a calculated distance equal to the error margin.

5. The method of claim 4 wherein the steps of calculating the error margin and compensating for the error margin is accomplished by using a software program.

6. The method of claim 1 wherein the step of applying the hysteresis brake involves rotation of the hysteresis brake.

7. A method for operating a mechanical drive system comprising:
   a. providing a drive train including a motor and a plurality of drive train components, the motor and drive train operable to move a driven component in a forward direction and a reverse direction;
   b. causing a hysteresis brake to resist movement of the drive train whenever the drive train moves the driven component both in the forward direction and in the reverse direction;
   c. calculating an error margin related to a distance of motor movement required to compensate for play between the drive train components when the direction of the driven component is reversed;
   d. receiving a requested direction of driven component travel and a requested distance of driven component travel;
   e. moving the motor sufficient to move the driven component the requested distance of travel when the drive train components are in positive engagement; and
   f. causing the motor to move the distance related to the error margin if the requested direction of driven component travel is opposite a previous direction of driven component travel.

8. The method of claim 7 further comprising the step of disregarding the error margin if the requested direction of driven component travel is the same as a previous direction of driven component travel.

* * * * *